United States Patent
Lawson

[19]

[11] Patent Number: 6,146,422
[45] Date of Patent: Nov. 14, 2000

[54] PROSTHETIC NUCLEUS REPLACEMENT FOR SURGICAL RECONSTRUCTION OF INTERVERTEBRAL DISCS AND TREATMENT METHOD

[76] Inventor: Kevin Jon Lawson, 2662 Edith Ave., Redding, Calif. 96001

[21] Appl. No.: 09/237,005

[22] Filed: Jan. 25, 1999

[51] Int. Cl.$^7$ ........................................... A61F 2/44
[52] U.S. Cl. ........................... 623/17.16; 623/17.11
[58] Field of Search ............................. 623/17.11, 17.12, 623/17.13, 17.14, 17.15, 17.16, 20.18

[56] References Cited

U.S. PATENT DOCUMENTS

| | | | |
|---|---|---|---|
| 5,047,055 | 9/1991 | Bao et al. | 623/17 |
| 5,306,308 | 4/1994 | Gross et al. | 623/17 |
| 5,401,269 | 3/1995 | Buttner-Janz et al. | 623/17 |
| 5,514,180 | 5/1996 | Heggeness et al. | 623/17 |
| 5,534,028 | 7/1996 | Bao et al. | 623/17 |
| 5,571,189 | 11/1996 | Kuslich | 623/17 |
| 5,645,596 | 7/1997 | Kim et al. | 623/17 |
| 5,645,597 | 7/1997 | Krapiva | 623/17 |
| 5,919,235 | 7/1999 | Husson et al. | 623/17 |
| 5,976,186 | 11/1999 | Bao et al. | 623/17 |

OTHER PUBLICATIONS

Casey K. Lee, et al, "Prosthetic Intervertebral Disc," Chapter 96, pp. 2007–2014, *The Adult Spine: Principles and Practice*: Raven Press, Ltd., New York, 1991.

*Primary Examiner*—V. Millio
*Assistant Examiner*—Alvin Stewart
*Attorney, Agent, or Firm*—Robert Charles Hill

[57] ABSTRACT

A prosthetic nucleus replacement comprises a solid flattened oval disk. The top surface of the disc is domed and has a crest that is about three times higher than the crest on the domed bottom surface. Both top and bottom surfaces are therefore convex. A peg extends down from the middle of the bottom domed surface and is used to pin the disc to the lower of two vertebrae it fits between. Metal markers are inserted into the peg and an outside edge of the disc so that radiographs can be used to determine the disc's in situ position. The prosthetic nucleus replacement is surgically implanted into the hollowed out intervertebral space through a flap cut in the natural annulus fibrosis. The lower vertebrae is prepared to receive the peg by clearing the material covering the top of the bone matrix. Bone cement is used around the peg to ensure a tight fit and immobile attachment of the disc to the lower vertebrae.

11 Claims, 2 Drawing Sheets

PROSTHETIC NUCLEUS REPLACEMENT FOR SURGICAL RECONSTRUCTION OF INTERVERTEBRAL DISCS AND TREATMENT METHOD

BACKGROUND OF THE INVENTION

1. Field of the Invention

The present invention relates to surgical methods and devices to treat back and leg pain and in particular to the surgical insertion of prosthetic nucleus replacement within the annulus fibrosis. The device replaces a portion of a damaged spinal intervertebral disc to restore function.

2. Description of Related Art

In the spine, the principal function of the disco-vertebral joint is to transmit compressive loads and still allow flexibility. Adjacent vertebrae are joined by a triple-joint complex. The anterior complex or column is formed by the vertebral bodies which are shaped like flattened cylinders with discoid shaped or ovoid shaped intervertebral discs sandwiched between each vertebral body. Facet joints in the rear of each vertebra have a smooth cartilage surface, lubricating joint fluid, and a covering capsule. The facet joints restrict the disc to small degrees of flexion and extension, limit rotation, and protect against translational shear stress. The disc itself comprises two principle parts, the nucleus pulposus at the core, and the annulus fibrosis, which is a multilayer bias-ply wrapping that surrounds the nucleus. The nucleus starts early in life as eighty percent water, and slowly desiccates with age.

A damaged disc can cause nerve dysfunction and debilitating pain in the back, legs and arms. Typical treatments that provide relief and allow patients to function again include back braces, medical treatment, physical therapy and surgery to remove the disc. A conventional surgical solution removes the bad disc and promotes new bone growth in the space to fuse the adjacent vertebrae together.

Several different prosthetic intervertebral disc devices are described by Casey K. Lee, et al., in "Prosthetic Intervertebral Disc," Chapter 96, *The Adult Spine: Principles and Practice,* Raven Press, Ltd., New York, © 1991. The conclusion of Lee, et al., is that "An appropriately designed and fabricated prosthetic intervertebral disc may provide an improved alternative to currently available surgical approaches to low back disorders." Lee, et al., describe their work at the orthopedic research laboratories at the New Jersey Medical School "to produce a prosthetic intervertebral disc design that has biomechanical characteristics similar to the natural disc." One result has been the manufacture of a unit with a nucleus, annulus, and end plates that are molded under heat and fused into a single prosthetic disc. However, success of such a device depends on solid bone attachment. Most prior concepts have been excessively complex and never used.

A prosthetic nucleus replacement can be surgically implanted within the annulus fibrosis. The natural attachments of the annulus would therefore be able to produce the requisite tensile strength of the repaired site. The prosthetic nucleus replacement would be subject primarily to compressive forces.

SUMMARY OF THE INVENTION

An object of the present invention is to provide a prosthetic nucleus replacement that is safer to surgically implant.

Another object of the present invention is to provide a prosthetic nucleus replacement that allows for x-ray images of the spine to be tracked over time and not interfere with diagnostic assessment.

Briefly, a prosthetic nucleus replacement embodiment of the present invention comprises a solid material flattened into an oval disk. The top surface of the disc is domed and has a crest that is about three times higher than the crest on the domed bottom surface. Both top and bottom surfaces are therefore convex. A peg extends down from the middle of the bottom-domed surface and is used to pin the disc to the lower of two vertebrae it fits between. Metal markers are inserted into the peg and an outside edge of the disc so that radiographs can be used to determine the disc's in situ position. The prosthetic nucleus replacement is surgically implanted into the hollowed out intervertebral space through a flap cut in the natural annulus fibrosis. The lower vertebra is prepared to receive the peg by clearing the material covering the top of the bone matrix. Bone cement is used around the peg to ensure a tight fit and immobile attachment of the disc to the lower vertebrae.

An advantage of the present invention is that a prosthetic nucleus replacement is provided that flexibly supports the normal compressive loads experienced by natural vertebrae.

Another advantage of the present invention is that a prosthetic nucleus replacement is provided that has a set of metallic markers that can assist a physician in determining the in situ orientation of said prosthetic nucleus replacement without obscuring normal anatomy or degrading future spinal imaging.

The above and still further objects, features, and advantages of the present invention will become apparent upon consideration of the following detailed description of specific embodiments thereof, especially when taken in conjunction with the accompanying drawings.

DETAILED DESCRIPTION OF THE INVENTION

Figure 1:
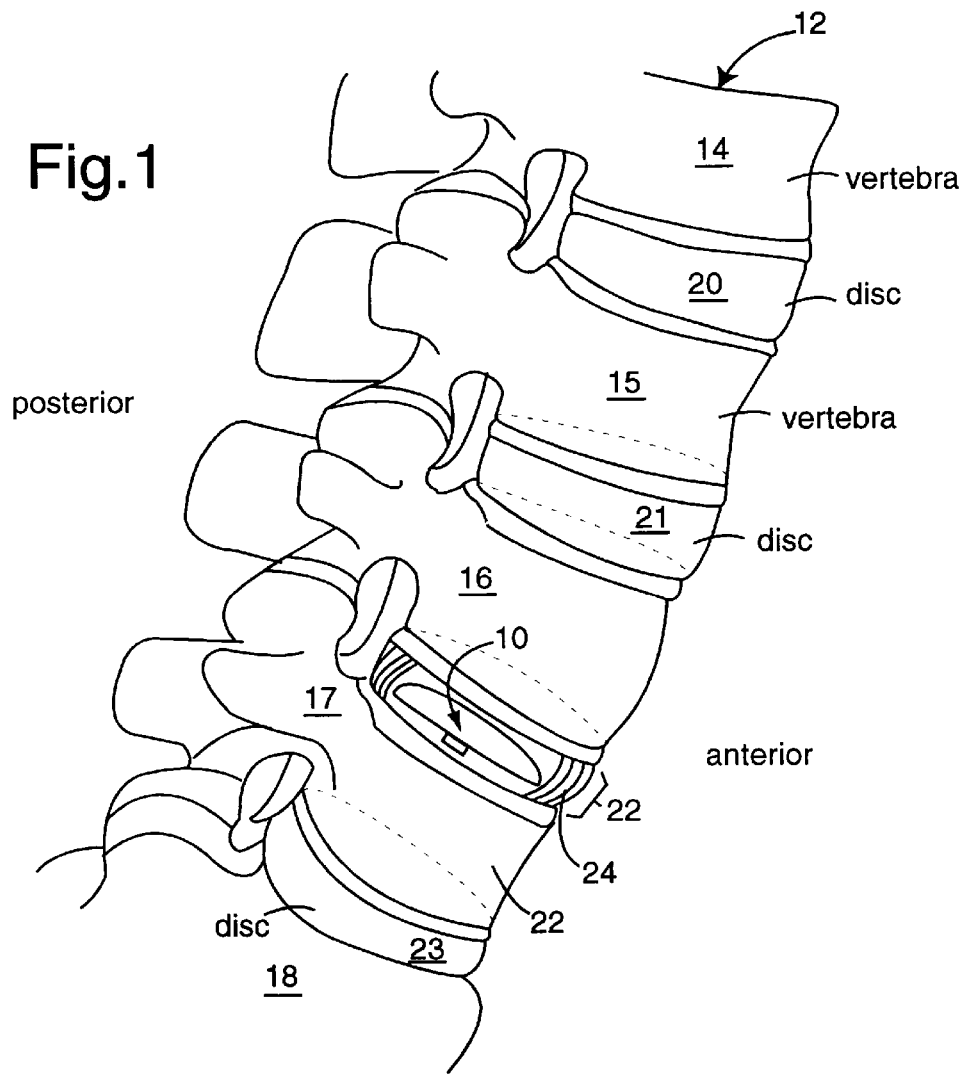
FIG. 1 is a diagram representing the spine of a patient with a prosthetic nucleus replacement embodiment of the present invention.

FIG. 1 illustrates a typical placement of a prosthetic spinal nucleus replacement embodiment of the present invention, referred to herein by the reference numeral 10. A human spine 12 commonly comprises a series of vertebrae 14–18 interdigitated with a corresponding series of discs 20–23. Each natural disc comprises a nucleus pulposus surrounded and contained by a corresponding annulus fibrosis. Natural nucleus pulposus have jelly-like structures that can absorb and dampen compressive shock loads. Natural annulus fibrosis structures comprise multiple layers of bias-ply filaments set at forty-degree angles that resemble the construction of an automobile bias-ply tire carcass.

Disc 22, between vertebra 16 and 17, is assumed in FIG. 1 to be degenerated. The spinal nucleus replacement prosthesis 10 is surgically embedded in the inter-vertebral space between vertebra 16 and 17, and inside an annulus fibrosis 24.

Prosthetic nucleus replacement embodiments of the present invention may comprise a solid polymer flattened into an oval disk. In general, any solid biocompatible material can be used, including various polymers and plastics, titanium, stainless steel, tantalum, chrome cobalt alloys, etc. Ultra-high molecular-weight polyethylene is presently preferred so that metal radiograph markers may be strategically placed in the nucleus replacement prosthesis 10.

Figure 2A:
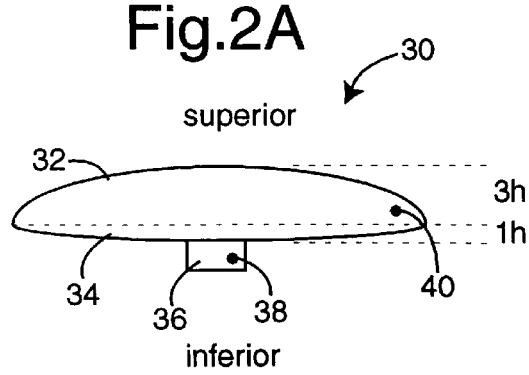
FIGS. 2A and 2B are an on-edge view and a bottom view of a prosthetic nucleus replacement embodiment of the present invention similar to that shown in FIG. 1.

As shown in FIG. 2A, a nucleus replacement prosthesis 30 has a top half 32 that is domed and has a crest that is about three times higher ("3h") than the crest ("1h") on a domed bottom half 34. The whole resembles an ellipsoid that has partially collapsed. Both top and bottom surfaces are therefore convex. The outside diameter of the nucleus 30 replacement prosthesis 30 can vary, e.g., in the range of twenty to thirty-six millimeters. The overall height can also vary, e.g., in the range of eight to sixteen millimeters. The actual dimensions required depend on the size of the patient and the exact site to receive the implant. Such required sizes are discernable from patient radiographs, CT-scans, and MRI-scans.

A peg 36 extends down from the middle of the bottom-domed surface 34. The peg 36 is typically two to four millimeters long and is used to pin the nucleus replacement prosthesis 30 to the lower vertebrae, e.g., vertebrae 17 in FIG. 1. A pair of metal radiograph markers 38 and 40, e.g., one in the peg 36 and one on an outside edge, are placed so that radiographs can be used to determine the disc's in situ position. The prosthetic nucleus replacement 30 is surgical implanted into the hollowed out intervertebral space through a flap cut in the natural annulus fibrosis. Such "hollowing out" is commonly called a diskectomy. The lower vertebra is prepared to receive the peg 36 by clearing the material covering the top of the bone matrix. Bone cement is used around the peg 36 to ensure a tight fit and immobile attachment of the disc to the lower vertebrae.

Figure 2B:
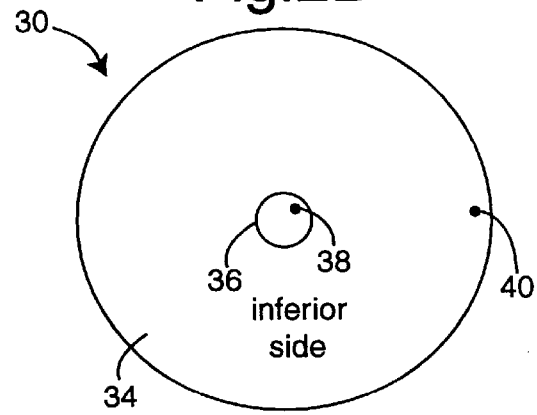
Figure 3A:
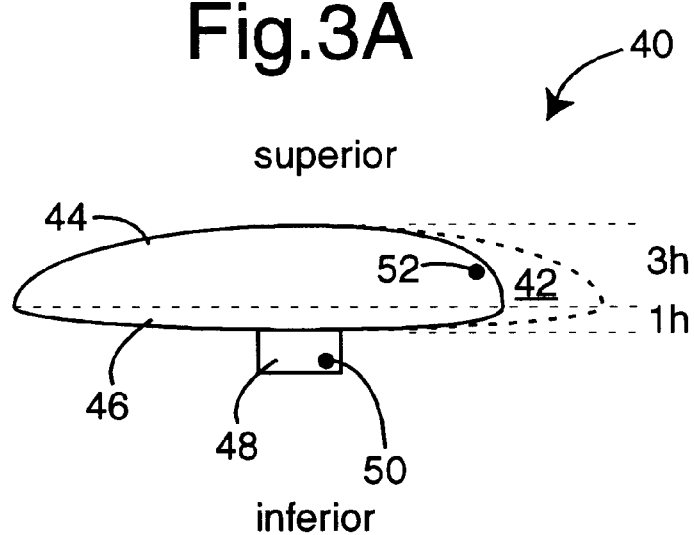
FIGS. 3A and 3B are an on-edge view and a bottom view of an alternative prosthetic nucleus replacement embodiment of the present invention in which one edge segment has been truncated.
Figure 3B:
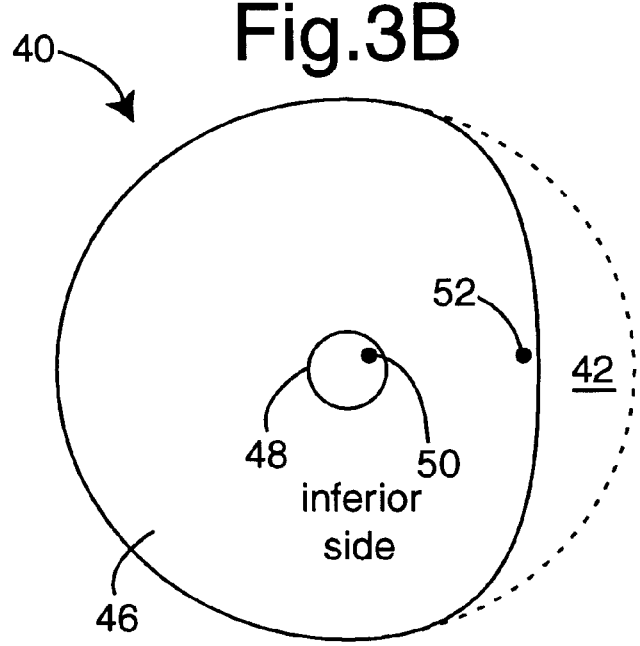

FIGS. 3A and 3B show a variation on the embodiment of FIGS. 2A and 2B. A nucleus replacement prosthesis 40 has an edge segment 42 removed from an otherwise oval or round lateral shape. This truncated part 42 is oriented in situ to face the spine posterior. A top half 44 of the main body is domed and has a crest that is about three times higher ("3h") than the crest ("1h") on a domed bottom half 46. Both top and bottom surfaces are convex, and at least the top surface shape mimics a natural nucleus. The outside major diameter of the nucleus replacement prosthesis 40 can vary, e.g., in the range of twenty to thirty-six millimeters. The overall height can also vary, e.g., in the range of eight to sixteen millimeters. The actual dimensions required depend on the size of the patient and the exact site to receive the implant. Such required sizes are discernable from patient radiographs, CT-scans, and MRI-scans.

A device similar to the nucleus replacement prosthesis 10, 30, and 40 was used by the present inventor, Kevin Lawson, M.D., in a recent surgical procedure. The patient was a sixty-four-year-old lady with a number of years of back pain, gradually worsening, along with leg pain and inability to ambulate distance. Plain x-rays, standing versus supine, showed a mobile spondylolisthesis of L4-5. Discography revealed painful L2-3 and L3-4 disks with an annular leak of contrast and reproduction of concordant pain. The L5-S1 disc was without pain. The L4-5 level was moderately painful and stenotic.

The risks and benefits of surgery were reviewed with the patient and she wished to proceed with intervention. Non-operative treatment had been ineffective, and her symptoms were worsening. An anterior disc reconstruction of the L2-3 and L3-4 levels was recommended to the patient because of the patient's obesity, general health condition, and smoking history. The alternative was a solid fusion with its attendant stiffness. Posterior L4-5 fusion and decompression was recommended. The patient was briefed concerning anterior interbody fusion at L3-4 and L2-3 with concomitant fusion posteriori from L2 to L5. Segmental instrumentation was reviewed with her as well as the FDA regulatory status of various spinal implants. The patient was informed that this was a novel and non-standard procedure, wherein standard orthopedic implants intended for use in non-spinal applications would be fashioned for use.

The patient was brought to the operating suite. After the induction of satisfactory general anesthetic and application of appropriate intravenous (IV) access, including a central venous line and an arterial line, the patient was carefully positioned on her right side with the left side up on a radiolucent extension of the operating table. A beanbag was positioned and compressed and the patient was secured in place. Anterior-posterior and lateral fluoroscopic images were confirmed. The patient's left prior nephrectomy incision was appropriate for the anterior diskectomy and reconstruction. The flank was prepped with sterile Betadine solutions and draped off with a sterile loban dressing and sterile drapes. The old incision was marked and incised longitudinally. Small vessels were cauterized with electrocautery. The incision was deepened down through the subcutaneous tissue and self-retaining retractors were placed. The external oblique muscle was divided longitudinally in line with its fibers and tagged with several heavy #1 VIC-RYL sutures. The internal oblique and transversalis muscle layers were adherent together and were divided in line with the incision across the grain of the muscle.

The retroperitoneal space was then identified and retroperitoneal fat easily identified. This was then dissected free and the wound separated and opened up from slightly beyond the mid axillary line anterior to the flank area. The retroperitoneal contents were dissected out bluntly with a sponge stick, RAY-TEC sponges and a malleable retractor. An OMNI retractor was then attached to the table and appropriate blades placed. The psoas muscle was identified and the fernoral nerve branches identified and protected.

The disc space was identified with a peanut dissector. Fluoroscopy was used to confirm appropriate level and the L3-L4 disc was marked with a spinal needle. Appropriate anterior-posterior-images and lateral images were obtained. The anterior-posterior-image allowed the surgical team to localize the middle of the vertebral body. The muscle was brushed back and retracted with a large PLIG nerve root retractor. The superior edge of the L4 vertebral body was chiseled away, breaking off a flake of bone with the annulus across the superior lateral edge of the L4 vertebral body. This was then folded up and the disc space evacuated with pituitary rongeurs and then with Japanese grabber rongeurs. Under fluoroscopic observation, a large angled spinal curet was used to curet the inferior disc space cartilaginous end plate and to curet a divot, or small perforation, in the end plate in the center and slightly posterior portion of the end plate. This was then checked in a trial. A twenty-three by eight-mm implant was used and impacted in position and then extracted later.

Attention was taken to the L2-3 disc space where the exposure was constrained. A simple annulotomy in a rectangular fashion was use with a distal trap door and that was then folded out. The degenerated disc was evacuated with pituitary rongeurs and severely disrupted disc fragments were removed. The distal end plate was curetted and a perforation made in the central divot portion.

The disc spaces were distracted with smooth ten-mm and eight-mm PLIG instruments. Each one was checked and a trial implant was able to be impacted in position. A twenty-six by nine-mm height PROFLIC-FIX patellar implant was selected for the L3-4 disc and a twenty-three-mm PROFLIC-FIX patellar implant from a RICHARDS set was selected for the L2-3 disc space. Both implants were prepared. The posterior aspect of the twenty-six-mm implant was trimmed away with a small high-speed bur and double-action rongeur to smooth the posterior aspect flat across and to decrease the anterior-posterior dimensions to about twenty-three-mm.

PALACOS bone cement and antibiotic powder were mixed and prepared into a dough paste and pushed into the inferior aspect of the implants adjacent to the peg and a cement retaining groove and then aligned with the disc space. The annulus flap was folded upward. The assembly was pressed into the disc space at L3-4 with appropriate retractors using a KOCHER clamp on the non-articular side edges of the implant. A bone impactor was used on the other edge to finish tapping it all into proper alignment in the disc space. Anterior-posterior and lateral images were checked and confirmed that the marker positioned the implant approximately in the mid portion of the disc space right to left in a slightly anterior-posterior direction. A twenty-three-mm implant was similarly prepared with a small amount of PALACOS bone cement and impacted into a center position within the disc space.

The annulus was repaired at the L2-3 level with #0 TYCRON sutures using a hernia-type needle through the residual annulus and end plate at the L3 body, grabbing the annulus attached to the L2 body, and repairing this with several interrupted sutures. Similarly, the flake of bone was repaired back with #0 ETHIBOND-type suture and two STAYTAC suture anchors from L3 to L4.

The wound was irrigated and suctioned dry throughout the procedure. Intermittent irrigation was done to maintain tissue hydration. There was no significant bleeding. The segmental vessels were carefully protected during the procedure and none were ligated or transected. A small amount of GELFOAM soaked with THROMBIN was applied to the areas of the annulus adjacent to the psoas muscle, which was allowed to fall back into its normal position in both locations. The retroperitoneal contents were allowed to fall back into their normal location. The OMNI retractor was removed. The deep transversalis layer and internal oblique layer were closed with several interrupted and then a running #1 VICRYL suture. The external oblique layer was then closed with a separate running #1 VICRYL suture. The subcutaneous tissue was closed with interrupted #2-#0 VICRYL sutures and the final skin closure of the flank incision was done with staples. XEROFORM, 4×8's, and foam tape were applied for a dressing. The drapes were removed and the first stage of the procedure was completed. The second stage comprised a standard decompression and fusion of another part of the spine.

In summary, the prosthetic nuclei of the present invention are generally implanted using a straight anterior or anterior lateral approach with incision of the anterior longitudinal ligaments of the annulus. A flap technique is used for the incision of the annulus, and such tissues are repaired with conventional sutures or suture anchors to the bone. The endplate cartilage of the superior vertebrae is preserved for permanent articulation with the implanted nucleus prosthetic. The endplate cartilage of the inferior vertebrae is curetted down to bone. The bone is prepared to receive a peg embedded in the implanted nucleus prosthetic. Such pinning and also cement are used to permanently immobilize this interface. The whole assembly is carefully centered as far posterior as possible to help reestablish natural kinematics of flex-extension and lateral bending.

In the construction of embodiments of the present invention, no attempt is made to reproduce the compression dampening qualities of the natural disc. Therefore, solid materials can be used in the fabrication of the main body ellipsoid.

Although particular embodiments of the present invention have been described and illustrated, such was not intended to limit the invention. Modifications and changes will no doubt become apparent to those skilled in the art, and it was intended that the invention only be limited by the scope of the appended claims.

What is claimed is:

1. A prosthetic nucleus replacement for implanting within an annulus fibrosis in one part of a human spine, comprising:
   an ellipsoidal body having a convex top side for contracting and articulating with an end-plate cartilage of a superior vertebrae and a convex bottom side for an immobile contact with an inferior vertebrae;
   said convex top side having a dome crest that exceeds a dome crest of said convex bottom side by a factor of a approximately three; and
   a peg extending from said bottom side of the ellipsoidal body and providing for a pinning action with respect to said inferior vertebrae.

2. The prosthetic nucleus replacement of claim 1, wherein:
   the ellipsoidal body comprises ultra-high molecular-weight polyethylene.

3. The prosthetic nucleus replacement of claim 1, further comprising:
   a set of metallic markers strategically placed within the ellipsoidal body and the peg, and that can assist a physician in determining the in situ orientation of said prosthetic nucleus replacement.

4. The prosthetic nucleus replacement of claim 1, further comprising:
   cement to help fix and immobilize said prosthetic nucleus replacement to said inferior vertebrae.

5. The prosthetic nucleus replacement of claim 1, wherein:
   the ellipsoidal body has an anterior edge and a posterior edge with one edge truncated so that such blunted end can be oriented in situ to face the spine posterior.

6. A method for surgically correcting a degenerated nucleus pulposus by the implantation of a prosthetic in a human spine, the method comprising:
   a flap technique incision of an annulus fibrosis corresponding to an affected area of a spine;
   a diskectomy of a degenerated nucleus pulposus in said affected area;
   curetting of cartilage down to the bone of an inferior vertebrae adjacent to said affected area and preparing said bone to receive a pin;
   inserting a solid ellipsoidal body that mimics a natural nucleus pulposus into said affected area through an incision in said annulus fibrosis;
   immobilizing said solid ellipsoidal body with respect to said inferior vertebrae; and repairing incision in said annulus fibrosis;

wherein, a permanent articulation between said solid ellipsoidal body and a superior vertebrae exists after surgery.

7. The method of claim 6, wherein:

the step of inserting is such that said ellipsoidal body has a convex top side with a dome crest that exceeds a dome crest of a convex bottom side by a factor of approximately three.

8. The method of claim 6, wherein:

the step of inserting is such that said ellipsoidal body comprises ultra-high molecular-weight polyethylene.

9. The method of claim 6, further comprising:

the step of inserting is such that said ellipsoidal body has a set of metallic markers strategically placed within the ellipsoidal body and the peg to assist a physician in determining an in situ orientation of said prosthetic nucleus replacement.

10. The method of claim 6, further comprising the step of:

cementing said ellipsoidal body to help fix and immobilize said prosthetic nucleus replacement to said inferior vertebrae.

11. The method of claim 6, wherein:

the step of inserting is such that said ellipsoidal body has one edge segment that has been truncated so that such blunted end can be oriented in situ to face the spine posterior.

* * * * *